United States Patent
Breton

(10) Patent No.: US 6,537,787 B1
(45) Date of Patent: Mar. 25, 2003

(54) ENZYMATIC METHODS FOR POLYUNSATURATED FATTY ACID ENRICHMENT

(76) Inventor: Gildas Breton, Penanguer, Concarneau (FR), F-29900

(*) Notice: Subject to any disclaimer, the term of this patent is extended or adjusted under 35 U.S.C. 154(b) by 0 days.

(21) Appl. No.: 08/737,098

(22) PCT Filed: Feb. 13, 1996

(86) PCT No.: PCT/FR96/00226
§ 371 (c)(1),
(2), (4) Date: Mar. 13, 1998

(87) PCT Pub. No.: WO96/26287
PCT Pub. Date: Aug. 29, 1996

(Under 37 CFR 1.47)

(30) Foreign Application Priority Data

Feb. 24, 1995 (FR) .............................................. 95 02153

(51) Int. Cl.⁷ .................................................. C12P 7/64
(52) U.S. Cl. ..................... 435/134; 554/169; 554/227
(58) Field of Search .......................... 435/134; 554/227, 554/169

(56) References Cited

PUBLICATIONS

Chem. Abstr., 104:147186, 1986.*
Chem. Abstr., 104:147187, 1986.*
Chem. Abstr., 112:75312, 1990.*
Chem. Abstr., 116:36796, 1992.*
Chem. Abstr., 113:114028, 1990.*

* cited by examiner

Primary Examiner—Deborah D. Carr
(74) Attorney, Agent, or Firm—Bierman, Muserlian and Lucas

(57) ABSTRACT

A process for obtaining polyunsaturated fatty acid concentrates comprising subjecting a fish oil containing docosahexaenoic acid (DHA) and eicosapentaenoic acid (EPA), to a selective enzymatic hydrolysis in position 1, 3 or 2, to obtain a mixture of free fatty acids, monoglycerides and diglycerides, separating the constituents of this mixture, collecting the free fatty acids which are purified by crystallization from urea, to increase the EPA and DHA content, decomplexing the isolated fatty acids by an inter-esterification between the free fatty acids concentrated into polyunsaturated fatty acids and the crude oil, in the presence of a lipase specific for position or steric hindrance, to obtain a mixture enriched with polyunsaturated fatty acid triglycerides which is separated and freed from the free fatty acids and a process for enrichment with polyunsaturated fatty acids (EPA, DHA) of phospholipids by an enzymatic route, as well as in the synthesis of monoacylglycerols of polyunsaturated fatty acids of the n3 series, by enzymatic synthesis starting with a 1,2-dialkylene glycerol which are useful in the domain of foodstuffs, cosmetics and pharmacology.

20 Claims, 2 Drawing Sheets

ENZYMATIC METHODS FOR POLYUNSATURATED FATTY ACID ENRICHMENT

This application is a 371 of PCT/FR96/00226 filed Feb. 13, 1996.

FIELD OF THE INVENTION

A subject of the present invention is new processes for the production of polyunsaturated fatty acid esters in a pure or concentrated form.

A more particular subject of the invention is processes for the production of esters of polyunsaturated fatty acids of the ω-3 series starting with glycerides of fatty acids extracted from fish oils, phospholipids, or 1,2-dialkyene glycerols, using an enzymatic treatment.

A specific subject of the invention is a process for the production of glycerides of polyunsaturated fatty acids in a pure or concentrated form from fish oil or other sources, characterized in that it allows, by enzymatic treatment, a mixture to be obtained containing a high content of docosahexaenoic acid (DHA) and/or of eicosapentaenoic acid (EPA), which can reach, in the case of fish oils, 60%.

Also a subject of the invention is a process for the production of glycerides of polyunsaturated fatty acids, characterized in that phospholipids whose EPA and/or DHA content represents about 50% of the total fatty acids are obtained from natural phospholipids, in the presence of polyunsaturated fatty acids, by enzymatic treatment.

The invention also relates to a process for the production of synthetic glycerides, characterized in that a 1,2-dialkylene glycerol is subjected to an enzymatic action in the presence of concentrated or pure polyunsaturated fatty acids, in order to obtain a monoacylglyceride whose EPA and DHA content represents at least 70% of the total fatty acids.

The invention relates in particular to a process for obtaining polyunsaturated fatty acid concentrates which consists of subjecting a fish oil containing DHA and EPA to a selective enzymatic hydrolysis, in position 1,3 or 2, in order to obtain a mixture of free fatty acids, monoglycerides and diglycerides, separating the constituents of this mixture, collecting the free fatty acids which are purified by crystallization from urea, in order to increase the content of EPA and/or DHA, decomplexing the isolated fatty acids, carrying out an inter-esterification between the free fatty acids, concentrated into polyunsaturated fatty acids, and the crude oil, in the presence of a lipase specific for position or steric hindrance, in order to obtain a mixture enriched with polyunsaturated fatty acid glycerides, which is separated and freed from the free fatty acids.

In a preferred manner, sardine oil is used which is obtained by pressing fresh sardines caught in cold waters. The sardine offers the advantage of an easy and constant supply. On the contrary, tuna vagina bulbi oil, which is industrially exploited, although it has a higher EPA and DHA content, has the disadvantage that the supply of raw material is limited.

The effect of the initial enzymatic hydrolysis is to split the ester function of the glycerol esterified by a polyunsaturated acid and to leave intact the other ester functions according to Diagram A.

It is also possible to hydrolyze the triglycerides present in sardine oil by a non-specific lipase so as to obtain a mixture of free fatty acids in which the polyunsaturated fatty acids represent about 30% of the total mixture. This mixture of fatty acids is fractionated by physical means in order to give a mixture in which the polyunsaturated fatty acids and in particular EPA and DHA predominant, which can be up to 70–80% of the mixture of free fatty acids.

The free polyunsaturated fatty acids are reesterified in the presence of an enzyme and in particular in the presence either of a non-specific lipase or a lipase specific for position 2.

If a non-specific lipase is used, the glycerol will be reacted with the mixture of polyunsaturated free fatty acids and a triglyceride is obtained whose polyunsaturated fatty acid content is of the order of 60%.

If, using a lipase specific for position FA.2, a mixture of already-concentrated polyunsaturated fatty acids and a glyceride esterified in a single position by a polyunsaturated fatty acids in inter-esterified, a 1,2-diglyceride can be obtained in which only two positions are esterified by a polyunsaturated fatty acid.

It is also possible to hydrolyze a triglyceride, position 2 of which is esterified by a polyunsaturated fatty acid using a specific enzyme and in particular by a lipase of SN.2-specific type, in order to obtain a mixture of free polyunsaturated fatty acids, monoglycerides and diglycerides having a polyunsaturated fatty acid content comprised between 80 and 100%.

After fractionation of this mixture, the free fatty acids are purified by cold crystallization in the present of urea, in order to increase the EPA and DHA content. This concentrated mixture is then subjected to an inter-esterification by a triglyceride, position 2 of which is occupied by a polyunsaturated fatty acid, and positions 1,3 of which are occupied by a saturated fatty acid, in the presence of a 1,3-specific lipase, so as to obtain a triglyceride at least two hydroxyls of which are esterified by a polyunsaturated fatty acid.

The invention also relates to a synthesis process for triglycerides enriched with non-saturated fatty acids, which consists of saponifying fish oil by chemical route or by enzymatic route, in order to obtain a mixture of saturated and non-saturated fatty acids, converting the saturated fatty acids into lower alkyl esters in the presence of a selective lipase in order to obtain a mixture of alkyl esters of saturated fatty acids and of non-saturated fatty acids, separating the alkyl esters of the saturated fatty acid, collecting the free non-saturated fatty acids and reacting these fatty acids with glycerol in the presence of a specific lipase in order to obtain a mixture of triglycerides enriched with polyunsaturated fatty acids.

The attached diagrams illustrate these different variants of the process.

The enrichment of the crude sardine oil, by extraction of the polyunsaturated fatty acids (PUFA), from an average content of 30% to a fatty acid content corresponding to 50–60% of the total can be brought about according to one of the two schematized processes (A and B) according to the invention.

Until recently, the majority of the production of fish oil, considered to be a by-product of processing, was intended, after hydrogenation, for the production of magarine. The low added value of the product and the use of physico-chemical treatments for extraction, deodorization, decolouration and hydrogenation involving destruction of the properties of the oil, explains the lack of interest of manufacturers in this type of process.

The principle characteristic of fish oils is their high natural content (20–30%) of polyunsaturated fatty acids, of ω 3 types, and in particular of docosahexaenoic acid (DHA) and eicosapentaenoic acid (EPA). At present, fish oil is the only commercially-exploitable source of long chain polyunsaturated fatty acids, despite production attempts using microbiological processes.

Since the epidemiological studies reported by Bang et al in 1971, and the physiological studies on this subject, it has become apparent that the essential fatty acids are the principle constituents of the phospholipids of the retina, of grey matter, of the epidermis; they play an important role in the central nervous system and have significant pharmacological properties in cardio-vascular diseases, as antithrombotics. Consequently, the interest shown by the pharmaceutical, cosmetic and parapharmaceutical industries has given rise to a fast-expanding market, in the USA, in JAPAN and in EUROPE. The PUFA (polyunsaturated fatty acids) market, based on the quality of the oils and therefore the added value, has 3 areas of use:

- crude oils, up to 30% of PUFA, for uses in the agricultural and food industry (AFI), oleochemistry, biopolymers, animal fodder.
- enriched oils, with 30 to 60%, for pharmaceutical and cosmetic uses.
- purified PUFA's, with 80 to 98%, for pharmacology.

At present, the grounds for objection of the fish oil industry reside at different levels, taking into account these new markets.

- quality of the raw material
- stability of the technical characteristics during the year, therefore necessitating a selection of the oils
- extraction methods to be reconsidered
- definition of the refining conditions as a function of requirements
- storage conditions Fish oils, sardine or cod liver, contain on average 20 to 30% of EPA+DHA relative to the total fatty acids. Among the wide variety of fish oils, the industrially-exploited tuna vagina bulbi oils are characterized by a higher content, up to 40%, but the supply of raw material is the main limitation to its production. Although it is easier to purify PUFA's, free or in the form of ethyl esters, the requirements of the PUFA market, in particular pharmacology and cosmetics, relate exclusively to fatty acids in the natural form of triglycerides for reasons of efficiency. Starting with oils containing up to 30% of EPA and DHA, numerous techniques can be used on the crude oil, such as winterization, molecular distillation or crystallization using a solvent.

Due to the number of possible combinations of the position of the fatty acids on the triglycerides, it is necessary to use more complex techniques in order to obtain, from a crude oil, PUFA contents higher than 30%. However, the fractionation of the free or esterified fatty acids up to 65–80% is possible using a certain number of methods, such as extraction by supercritical fluid, complexing with urea, chromatography, separation on zeolite and even separation up to 90% is possible by HPLC.

Apart from these physico-chemical methods, enrichment by enzymatic route has been used with success on vegetable oils.

Physico-chemical techniques, due to their investment cost (for example 3MF for a 1 m³ industrial FSC extractor) can only be economically viable for enrichments greater than 80% characterized by a high added value. On the other hand, enzymatic techniques, which are more straightforward and therefore less costly, are in theory well suited to fill the gap between the crude oil and on oil titrating 55–60% PUFA.

In fact, for some years, numerous studies have shown the physiological and dietetic importance of polyunsaturated fatty acids and especially of eicosapentaenoic acid (or EPA=Δ-5, 8, 11, 14, 17-eicosapaentaenoic acid) and docosahexaenoic acid (or DHA=Δ-4, 7, 10, 13, 16, 19-docosahexaenoic acid). These compounds are only formed in the human body in very small quantities and the quantities produced according to the two biological diagrams hereafter carry on decreasing over the years, such that a deficiency may result in pregnant women and in elderly people. The diagram hereafter summarizes the formation pattern of polyunsaturated fatty acid in the body.

| n-6 | | n-3 | |
|---|---|---|---|
| 18:2 | Δ-9, 12 (linoleic acid) | 18:3 | Δ-9, 12, 15 (α-linolenic acid) |
| ↓ | Δ-6 desaturase | ↓ | |
| 18:3 | Δ-6, 9, 12 (γ-linoleic acid) | 18:4 | Δ-6, 9, 12, 15 (octadecatetraenoic acid) |
| ↓ | elongation | ↓ | |
| 20:3 | Δ-8, 11, 14 (dihomo-γ-linolenic acid) | 20:4 | Δ-8, 11, 14, 17 (eicosatetraenoic acid) |
| ↓ | Δ-5 desaturase | ↓ | |
| 20:4 | Δ-5, 8, 11, 14 (arachidonic acid) | 20:5 | Δ-5, 8, 11, 14, 17 (eicosapentaenoic acid) |
| ↓ | elongation | ↓ | |
| 22:4 | Δ-7, 10, 13, 16 (adronic acid) | 22:5 | Δ-7, 10, 13, 16, 19 (docosapentaenoic acid) |
| ↓ | Δ-4 desaturase | ↓ | |
| 22:5 | Δ-4, 7, 10, 13, 16 (docosapentaenoic acid) | 22:6 | Δ-4, 7, 10, 13, 16, 19 (docosahexaenoic acid) |

There are many uses of enzymes in the treatment of fish, production of protein hydrolyzates by proteases, silage making, breaking down of tuna, tenderizing of the flesh, hydrolysis of the tissues surrounding the eggs (caviar), elimination of the liver membranes. With regard to the oils, numerous publications show the usefulness of enzymatic treatments for extracting and purifying the polyunsaturated fatty acids. The most commonly used enzymes are lipases which either allow the triglycerides to be hydrolyzed into fatty acids and glycerol under aqueous conditions, or conversely the fatty acids to be esterified under anhydrous conditions or in the presence of organic solvents.

Numerous lipases hydrolyze the triglycerides according to the following sequence:

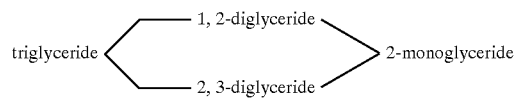

However, certain lipases do not respond to these kinetics due to the specific "recognition":

- of certain fatty acids
- of the position of these fatty acids on the triglyceride
- of glycerides of different molecular weights or
- of their stereospecificity.

Thus numerous lipases of different specificities exist:

- intestinal lipases or lipases of panniculus adiposus, of insect muscle, which preferably hydrolyze the monoglycerides rather than the triglycerides.
- lipases of Mucor, Rhizopus, mil, and porcine pancreatic lipase, which are specific for positions 1,3 on the triglyceride, whilst the lipase of Pseudomonas is specific for position 2.
- lipase of Candida which preferably hydrolyzes the ester bonds of DHA.

lipase of cabbage (*B. napus*) which recognizes the position of the double bond on the fatty acids and differentiates -linolenci acid from DHA, or lipase of Geotrichum which is specific for fatty acids containing CIS-9 and CIS-9 -CIS-12 unsaturations.

This specificity of the lipases is generally the basis of the fractionation processes for commercially useful fatty acids contained in vegetable or fish oils.

Thus the following enrichment processes have been described: of α-linolenic acid in a primrose oil (from 9.5% to 64.6%) with a cabbage lipase; of DHA in a cod liver oil (from 12.7 to 45.9%) with a Mucor lipase; of EPA+DHA in a cod liver oil (from 23 to 72.2%) with a Mucor lipase; of DHA in a tuna oil (concentration factor=3) with a Candida lipase; of 5-eicosaenoic acid (20:1) in a Meadowfoam oil (from 83.5 to 95%) by a Chromabacterium lipase.

Schematically, the preparation of triglycerides enriches with PUFA is based on an inter-esterification catalyzed by a selective lipase:

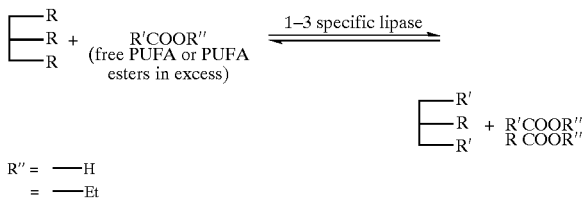

However, the prior enzymatic processes require a supply of free or esterified PUFA of high purity. Consequently, this supply must be preceded by a total hydrolysis of the triglycerides in order to release the free PUFA's by a lipase and by a purification by chemical route or using specific lipases.

There are particular difficulties which the present process aims to resolve.

Figure 1:
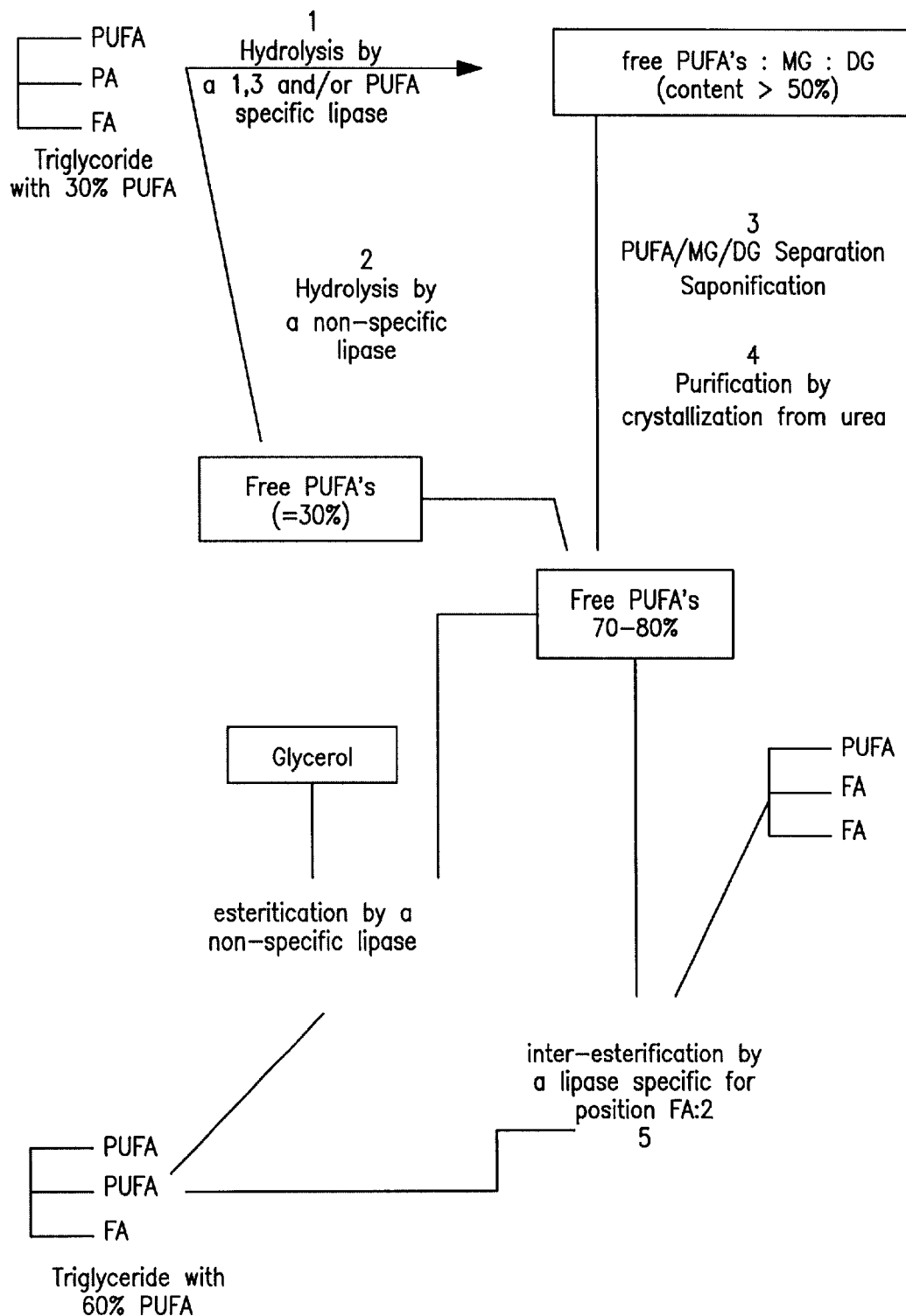
FIG. 1 is a flow sheet of one process of the invention.
Figure 2:
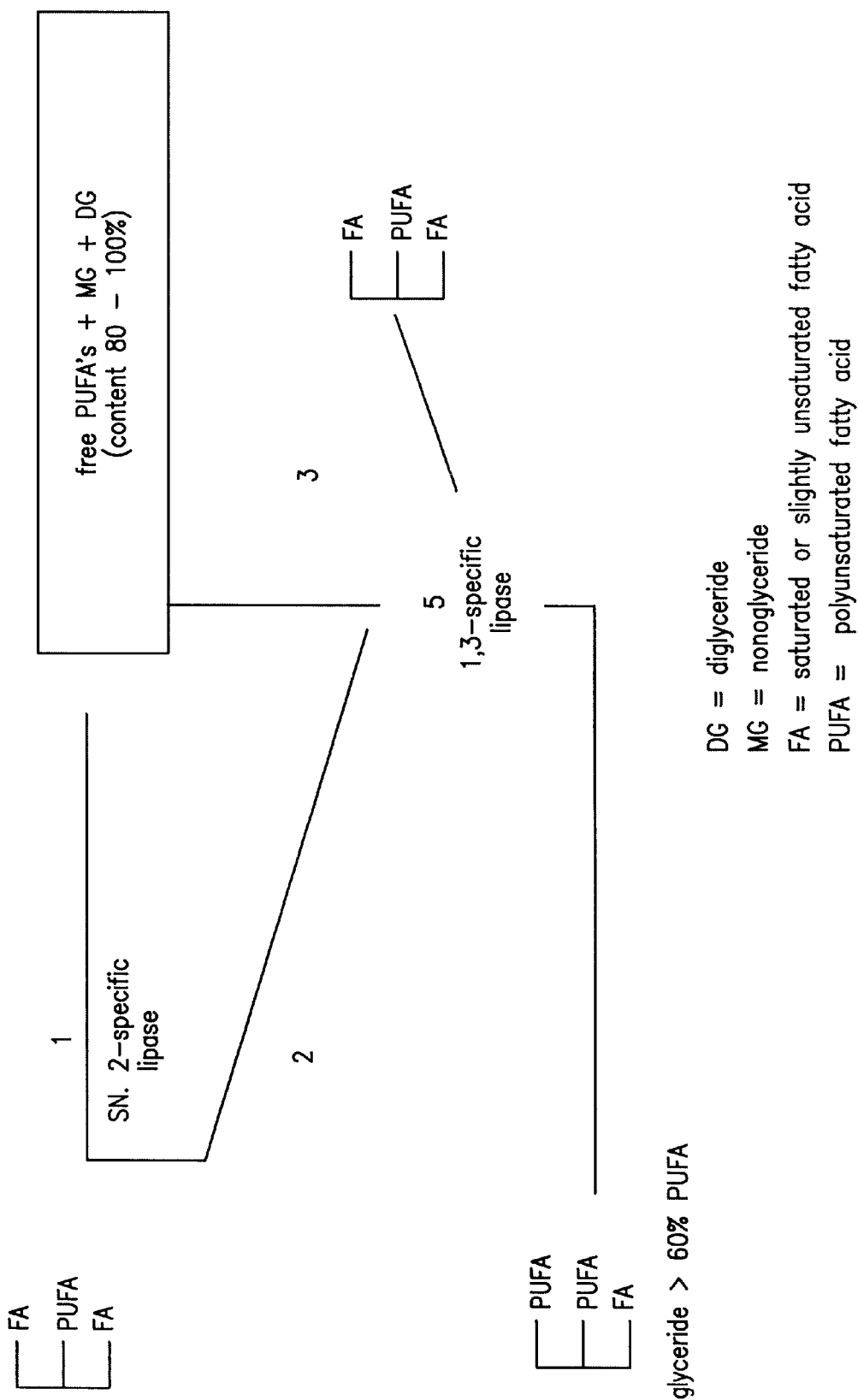
FIG. 2 is a flow sheet of a second process of the invention.

According to one of the processes of the invention, it is necessary to determine in advance the position of the polyunsaturated fatty acids in the triglycerides of treated sardine oil. According to the species, and perhaps according to the season, the polyunsaturated fatty acids are either in position 2, or in position 1,3. It is therefore necessary, after this determination, to chose a suitable lipase for the hydrolysis reaction as for the inter-esterification or trans-esterification reaction. The technique used to determine this position is based on the hydrolysis by specific enzymes and on the analysis by physical methods (GC, TLC or HPLC) of the EPA and DHA content in the hydrolysis products.

Using stocks of commercially-available enzymes (ectorasos and lipases), immobilized or not, hydrolysis tests were carried out to determine the optimum polyunsaturated fatty acid content so that the subsequent separation and purification stages are made easier.

The parameters studied were the following:
- choice of the enzymes as a function of their specificity: hydrolysis of the long chains of FA, hydrolysis of the short chains specifically, hydrolysis of the EPA and DHA bonds specifically
- water content (on which the kinetics of the reaction depends)
- oil/enzyme ratio
- temperature
- inhibition by the products of the reaction Using the results on the laboratory scale, a scale-up (factor 10) was experimented with in order to evaluate the cost-effectiveness of this phase.

These tests showed that three enzymes led to the best EPA/DHA ratios, namely:
- a lipase of Pseudomonas fluorescens
- a lipase of Mucor javanicus
- a lipase of Mucor miehei The results provide a content of triglycerides with polyunsaturated fatty acids of about 70%, with an EPA/DHA ratio of the order of 1.

In the following stage, the free fatty acids are separated from the other hydrolysis products (monoglycerides, diglycerides, glycerol) by washing with basic water or by saponification.

The third stage of the process consists of purifying the mixture of free fatty acids by cold crystallization in the presence of urea in an ethanolic medium.

The tests carried out showed that the $C_{20}$ or $C_{22}$ long chain fatty acids crystallized more easily cold (−10° C.) after complexing with urea and that in this way a useful concentration and yield of polyunsaturated fatty acids (from 63 to 83%) could be obtained. However, this technique, based on the differential solubility of the fatty acids in the solvent used, requires an adaptation to the desired polyunsaturated fatty acids and an optimization of the precipitation parameters (temperature, urea/polyunsaturated fatty acid ratios) and of the decomplexing conditions.

The saponification stage necessary for separating the free fatty acids from the other products of the enzymatic hydrolysis must meet precise experimental conditions, because it determines the effects of the hydrolysis products on the specific and non-specific lipases, on the separation yield and on the purification yield.

The inter-esterification stage of the crude oil by concentrated polyunsaturated fatty acids is an inverse enzymatic stage of the initial stage of the process according to the invention. It requires totally different experimental conditions for moving the reaction equilibrium and, in particular, the choice of water concentration, the optional presence of organic solvents or the choice of the pH and the concentrations. The concentrated polyunsaturated fatty acids are put in contact with the crude fish oil and with the chosen enzyme. The enzyme used is a lipase specific for the ester bonds which do not contain any polyunsaturated fatty acid, so that the ester bond combined with a polyunsaturated fatty acid present, initially, in the crude oil (±30%) is preserved.

The water content is preferably low and kept constant. The nature of the solvent, if there is one, is important. It must be compatible with the enzyme.

In a preferred manner, the enzyme used is a Mucor miehei lipase commercially-available under the name NOVOZYME 435 from the Novo Nordisk Company.

The enzyme used can be separated off at the end of the reaction and, optionally, reused. Separation and reuse are made easier by an immobilized enzyme.

After the inter-esterification reaction, the free fatty acids are separated by aqueous phase washings at a basic pH. The triglycerides formed do not pass into the aqueous phase and can then be taken up in a solvent. By evaporation, the desired concentrated mixture is obtained containing between 50 and 70% of polyunsaturated fatty acids.

Determination of the position of the polyunsaturated fatty acids on the triglycerides allows the choice between the two variants of the process to be made:

position 1,3 →process A
position SN.2 →process B

Also a subject of the invention is polyunsaturated fatty acid concentrates, rich in or enriched with heicosapentaenoic acid and docosahexaenoic acid, obtained by the process according to the invention. A subject of the invention is also triglycerides enriched with eicosapentaenoic acid and docosahexaenoic acid obtained by the inter-esterification process according to the invention.

A subject of the invention is also fish oils and in particular sardine oils enriched with or concentrated in EPA and/or DNA obtained according to the process of the invention.

The invention also relates to a process for enrichment with polyunsaturated fatty acids (EPA $C_{20:5n3}$, DHA $C_{22:6n3}$) of phospholipids by enzymatic route which consists of reacting one or several phospholipids with a PUFA of the n3 series in the presence of a lipase or order to obtain a modified phospholipid.

It consists of modifying the fatty acid composition of the phospholipids by the previously-described enzymatic process, that is by a trans-esterification reaction which reacts PUFA and phospholipids in the presence of a lipase.

The reaction can be schematized in the following way:

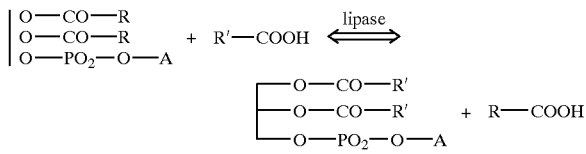

This trans-esterification is carried out in an organic solvent only in the presence of phospholipids, free fatty acids (PUFA) and the enzyme. However, certain studies seem to indicate that the use of solvents with a high dielectric constant encourage the inter-esterification of fatty acids (Hosokawa et al, 1995; Mustranta et al, 1994; Mutua et al, 1993). The presence of a molecular sieve (3 Å) which traps the water improves the trans-esterification of the PUFA's.

After reaction, it is necessary to purify the products, that is the free fatty acids of the phospholipid pool, for example by chromatography on a silica column or by any other separation technique (ex: ultrafiltration).

The phospholipids obtained have an EPA and DHA content of about 50% of the total fatty acids.

The phospholipids are important major constituents of the cell membranes. The fatty acid chains of which they are composed play an essential role at the level of membrane fluidity and more particularly the highly polyunsaturated fatty acid chains, amongst which are EPA and DHA, which allow the cell to function normally.

Furthermore, the phospholipids can be used in cosmetology (liposomes) and in the agricultural and food industry due to their amphilic character.

Also a subject of the invention is phospholipids enriched with or concentrated in EPA and/or DHA obtained according to the process of the invention.

Also a subject of the invention is the synthesis of PUFA ($\mu$3) monoacylglycerols by enzymatic synthesis starting with a 1,2-alkylene glycerol.

The process according to the invention consists of reacting PUFA's (n3) in the presence of a lipase (example: Mucor mieheï lipase) with glycerol two of the alcohol functions of which are blocked, by the route previously described for the enzymatic synthesis of the triglycerides.

The synthesis of the glyceric monoesters of PUFA n-3 (EPA, DHA) can be schematized in the following way:

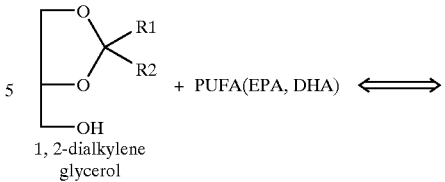

1, 2-dialkylene glycerol

1, 3-dialkylene 3-acyl glycerol

By reacting the purified PUFA's, containing at least 70% of EPA and DHA, it can be envisaged to obtain monoacylglycerides whose EPA and DHA represent at least 70% of the total fatty acids.

The monoglycerides are sought mainly for their emulsifying properties in the domain of cosmetics, pharmacology and the agricultural and food industry.

Also a subject of the invention is glyceric monoesters enriched with or concentrated in EPA and/or in DHA obtained according to the process of the invention.

It goes without saying that the processes of the invention can include numerous variants in order to be adapted to the various specific forms made necessary by the variability of the raw material and in particular fish oil in its fatty acid content and in the polyunsaturated fatty acid triglyceride and saturated fatty acid triglyceride ratios, without however exceeding the scope of the invention.

One or more stages of the processes described above can also be replaced by an extraction using a supercritical fluid such as for example supercritical $CO_2$.

EXAMPLE 1

Saponification: the triglycerides are saponified starting with an oil preferably rich in PUFA. The reaction is carried out in a basic ethanolic medium, for example 1 volume of sardine oil per 1 volume of the saponification mixture (⅓ water with 20% soda, ⅔ 99% ethanol), heated (70° C.) for about 30 minutes under an inert atmosphere.

After successive washing stages at an acid pH (passing the fatty acids in R—COOH form), the acids are recovered by phase separation.

Fractionation using urea: the ethanol is saturated with urea. This saturation allows problems relating to the fractionation temperature to be avoided.

The ratios of extraction are:

1 volume of oil/2 volumes of urea/6 to 8 volumes of ethanol

The enriched phase reaches values close to 85% to PUFA relative to the total fatty acids.

It is in this way that starting with a fish oil with 20% of PUFA, a fraction containing 70 to 75% of EPA+DHA relative to the total fatty acids was able to be obtained. The PUFA yields obtained by this process are close to 85%.

Results of enzymatic hydrolysis: the preferred positioning of the PUFA's on the glyceric skeleton is:

DHA preferably in β position at about 60% almost uniform distribution of EPA in α, βposition.

The result of the screening of the enzymes tested appears in the table hereafter.

In this initial data, no hydrolysis has been observed which enriches the free fatty acid fraction with EPA and/or DHA. On the other hand an increase of EPA and DHA in the monoacylglyceride fraction is noted.

The monoacylglycerides with a high content of omega 3 PUFA, produced, may constitute a possible marketing route. In fact, they would be more easily absorbed at the level of the intestinal wall then the triglycerides. Furthermore, the PUFA's are preferable in their monoacylglyceride form to their very oxidizable free form. According to its specificity, the lipase hydrolyzes the triglyceride either as a function of the positions on the glyceride or as a function of the steric hindrance of the fatty acids. Thus, the choice of the lipase used on the oil whose distribution of fatty acids on the glyceric skeleton is known, allows an influence to be exerted on the EPA/DHA balance, as a function of the intended use.

The fatty acids produced by the hydrolysis are eliminated by washing with basic water. According to this process, no solvent is used.

Results: Screening of the activity of the lipases on sardine oil

| Enzyme used | | Distribution after hydrolysis (% of the mass) T = 100 − % TG | PUFA EPA + DHA % | DHA/EPA balance | EPA + DHA material balance 100 g of oil in g | in % |
|---|---|---|---|---|---|---|
| Oil before hydrolysis | | free FA's = 0.28 | 20 | 1 | 20 | 20 |
| Eorcine pancreatic lipase | TC | 34.1 (T = 65) | 19.6 | 1.1 | 6.7 | 38.2 |
| | AG | 31.7 | 5.5 | 0.84 | 1.74 | 9.9 |
| | DAG | 20.2 | 25.3 | 1.0 | 5.1 | 29.3 |
| | MAG | 13.9 | 28.4 | 2.0 | 3.9 | 22.6 |
| Wheatgerm lipase | | T = 0 | | | | |
| Lipase of Pseudomonae fluorescens | AG | 67.7 (T = 100) | 10.3 | 1.6 | 7 | 34.4 |
| | DAG | 6.1 | 25.3 | 0.99 | 1.54 | 7.7 |
| | MAG | 26.2 | 44 | 1.1 | 11.5 | 57.6 |
| Lipase of Penicillium roqueforti | TG | 23.4 (T = 77) | 21.9 | 1 | 5.1 | 34.4 |
| | AG | 37.3 | 7.8 | 0.75 | 2.9 | 16 |
| | DAG | 32.4 | 25 | 1 | 8.1 | 44.8 |
| | MAG | 6.9 | 28.2 | 1.68 | 1.9 | 10.7 |
| Lipase of Candida cylindracea | TG | 64 (T = 36) | 20.9 | 1.2 | 13.4 | 34.4 |
| | AG | 16.8 | 3.8 | 1.1 | 0.64 | 3.4 |
| | DAG | 17.8 | 24.4 | 1.4 | 4.3 | 23 |
| | MAG | 1.5 | 31.7 | 1.3 | 0.47 | 2.5 |
| Lipase of Rhizopus delemar | AG | 68.1 (T = 100) | 10.1 | 0.48 | 6.9 | 35.7 |
| | DAG | 10.4 | 28.4 | 3.1 | 3.0 | 15.3 |
| | MAG | 21.4 | 44.2 | 3.3 | 9.5 | 48.9 |
| Lipase of Mucor javanicus | AG | 73.3 (T = 100) | 12.8 | 0.73 | 9.4 | 34.4 |
| | DAG | 4.5 | 21.2 | 2.2 | 0.95 | 4.9 |
| | MAG | 22.2 | 40.7 | 4.1 | 9 | 46.6 |
| Lipase of Mucor miehei | AG | 77.7 (T − 100) | 9.4 | 0.6 | 7.3 | 34.4 |
| | DAG | 6.5 | 38.3 | 2.7 | 2.5 | 14.7 |
| | MAG | 15.7 | 45.1 | 4 | 7.1 | 42 |
| Lipase of Rhizopus arrhizus | | T = 0 | | | | |
| Control | | T = 0 | | | | |

Results after hydrolysis and extraction of the MAG+DAG

| Enzyme | | Yield | % Distribution of the mass | DHA/EPA balance | % EPA + DHA | % EPA | % DHA |
|---|---|---|---|---|---|---|---|
| Pseudomonas fluorescens | DAG | | 19 | 0.99 | 25.3 | | |
| | MAG | | 81 | 1.1 | 44 | | |
| | Total | 32.3 | | 1.8 | 40.37 | 19.4 | 21 |
| Rhizopus delemar | DAM | | 33 | 3.1 | 28.4 | | |
| | MAG | | 67 | 3.3 | 44.2 | | |
| | Total | 31.8 | | 3.23 | 39.3 | 9.3 | 30 |
| Mucor javanicus | DAG | | 16.8 | 2.2 | 21.2 | | |
| | MAG | | 83.1 | 4.1 | 40.7 | | |
| | Total | 26.7 | | 3.78 | 37.3 | 7.8 | 29.5 |
| Mucor miehei | DAG | | 30 | 2.7 | 38.3 | | |
| | MAG | | 70 | 4 | 45.1 | | |
| | Total | 22.2 | | 3.62 | 43.2 | 9.35 | 33.9 |

Enzymatic grafting:
Example of esterification of the PUFA's on natural glycerol:
enzyme used: Novozyme 435
  15 hours at 45° C.
  elimination of the free fatty acids which have not reacted by basic washing
72% of triglycerides. Triglycerides+diglycerides=98%
DHA/EPA=0.65
EPA+DHA=68%
PUFA=83%

Taking account of the three synthesis routes, and with reference to the hydrolysis results of the different enzymes, this first route, that is hydrolysis followed by grafting, seems the most appropriate because it offers a greater flexibility in the modulation of the DHA/EPA ratio. Furthermore, the hydrolysis products, the majority of which are monoacylglycerides, could be used commercially.

Therefore, according to the lipase used, a mixture of mono- and diacylglycerides can be obtained with either a DHA/EPA balance of 1.1 with the lipase of *Pseudomonas fluorescence* or of 4 with the lipase of *Mucor mieheï*. Grafting of these mono- and diacylglycerides with purified PUFA's with a known DHA/EPA balance, using a non-specific enzyme (for example the preparation Novozyme 435 from the Company Novo Nordisk Bioindustries (UK) allows triglycerides rich in PUFA to be obtained.

It can be observed that monoacylglycerides rich in PUFA can be easily produced by enzymatic grafting of purified PUFA on natural glycerol.

Another possible route, that of an incomplete hydrolysis with simultaneous trans-esterification, may lead to an increase in the PUFA's on the triglycerides (Y. Shimada et al, 1994).

EXAMPLE 2 phospholipids (origin Lucas meyers soja base): 100 g
purified PUFA's (of which EPA, DHA): 110 g
Enzyme (immobilized lipozyme IM of Novo Nordisk): 20 g
Molecular sieve (3 Å): 3 to 5 g The reaction is carried out under an inert atmosphere, at a temperature of 45° C. with agitation. Prior hydration of the enzyme is advised. The reaction time is about 9 hours, after which oxidation of the existing PUFA's can lead to an inhibition of the lipases. The reaction products are then purified on a silica column.

The phospholipids obtained have an EPA and DHA content of about 46% of the total fatty acids. (Which must mean that only one of the two possible positions (α, β) can be esterified by EPA or DHA in the presence of the lipase Lipozyme IM).

What is claimed is:

1. A process for obtaining polyunsaturated fatty acid glyceride concentrates comprising subjecting a fish oil containing docosahexaenoic acid (DHA) and eicosapentaenoic acid (EPA), to a selective enzymatic hydrolysis in position 1, 3 or 2 to obtain a mixture of free fatty acids, monoglycerides and diglycerides, separating the constituents of this mixture, collecting the free fatty acids which are purified by crystallization from urea to increase the EPA and DHA content, decomplexing the isolated fatty acids, and carrying out an inter-esterification between the free fatty acids concentrated into polyunsaturated fatty acids and the crude oil in the presence of a position-specific lipase, to obtain a mixture enriched with polyunsaturated fatty acid triglycerides which is separated and freed from the free fatty acids.

2. The enrichment process of claim 1, with polyunsaturated fatty acid (EPA, DHA) of phospholipids comprising reacting polyunsaturated fatty acid (PUFA) of the n3 series and a phospholipid, in the presence of a lipase, to obtain a mixture of modified phospholipids and fatty acids, and separating the free fatty acids from the phospholipid pool by a standard separation technique to obtain a phospholipid of the formula:

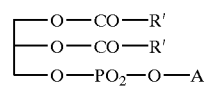

wherein R' is a PUFA(n3)
A is selected from the group consisting of ethanolamine, serine and choline.

3. The process for obtaining monoacylglycerides of polyunsaturated fatty acids (PUFA) of the n3 series of claim 1 comprising reacting PUFA's of the n3 series in the presence of a lipase with glycerol, two of the alcohol functions of which are blocked in ketal form to obtain a monoacylglyceride of the formula:

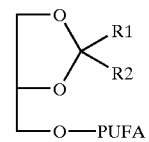

wherein R1 and R2 are lower alkyl and PUFA is polyunsaturated fatty acid of 2 to 6 double bonds.

4. The process of claim 1 wherein the fish oil containing DHA and/or EPA is sardine oil obtained by pressing sardines caught in cold waters.

5. The process of claim 1 wherein fish oil is subjected to an enzymatic treatment which non-selectively releases all the fatty acids present and the polyunsaturated fatty acids are isolated separately.

6. The process of claim 1 wherein the enzymatic treatment provides a mixture of monoglycerides, diglycerides and free fatty acids.

7. The process of claim 5 wherein the free fatty acids released are constituted mainly by polyunsaturated fatty acids.

8. The process of claim 5 wherein the free polyunsaturated fatty acids are concentrated by crystallization with urea, cold and in an ethanolic medium.

9. The process of claim 1 wherein the concentrated mixture of polyunsaturated fatty acids is inter-esterified with a triglyceride, position 2 of which is occupied by a polyunsaturated fatty acid in the presence of a 1,3-specific lipase to obtain a triglyceride at least two hydroxyls of which are esterified by a polyunsaturated fatty acid.

10. The process of claim 7 wherein the concentrated mixture of polyunsaturated fatty acids is reacted with glycerol in the presence of a non-specific lipase to obtain a diglyceride, two alcohol functions of which are esterified by a polyunsaturated fatty acid.

11. The process of claim 1 wherein a fish oil triglyceride, one position of which is esterified by a polyunsaturated fatty acid, is hydrolyzed by a non-specific enzyme to obtain a mixture of free polyunsaturated fatty acids, monoglycerides and diglycerides, fractionating the mixture, purifying the free fatty acids by cold crystallization in the presence of urea to increase the EPA and DHA content, subjecting the concentrated mixture to an inter-esterification with a triglyceride at least one position of which is occupied by a polyunsaturated acid in the presence of a lipase specific for position 2 to obtain a triglyceride with a high polyunsaturated fatty acid content.

12. The process of claim 1 wherein reacting a fish oil triglyceride, one of the hydroxyl functions of which is esterified by a polyunsaturated fatty acid, with a 1,3-specific lipase, to obtain a mixture of polyunsaturated fatty acid, mono- and diglycerides, reacting the mixture with a triglyceride of which only position 2 is blocked by a polyunsaturated fatty acid in the presence of a 1,3-specific lipase to form a triglyceride, at least two alcohol functions of which are esterified by an acyl group derived from a polyunsaturated fatty acid.

13. A process of claim 12 wherein the non-specific enzyme is chosen from a lipase of Pseudomonas fluorescens, a lipase of *Mucor javanicus* and a lipase of *Mucor miehei*.

14. The process of claim 12 wherein the specific enzyme is a lipase of *Candida antartica*.

15. The enrichment process of claim 2 with PUFA of phospholipids wherein the specific enzyme is a lipase of *Mucor miehei*.

16. The enrichment process of claim 2 with PUFA of phospholipids wherein the enzymatic hydrolysis is carried out in the presence of a molecular sieve.

17. The process of claim 3 with PUFA (n-3) monoaclyglyceride comprising reacting a blocked 1,2-dialkylene glycerol in the presence of a lipase with a polyunsaturated fatty acid (PUFA) to obtain a 1,2 dialkylene 3-acyl glycerol of the formula:

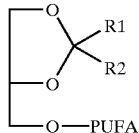

wherein PUFA is a polyunsaturated fatty acid having 2 to 6 double bonds and

R1 and R2 are individually lower alkyl.

18. The process for obtaining PUFA (n3) monoacylglycerides of claim 3 comprising subjecting a 1,2-alkylidene glyceride to a hydrolysis in acid medium to form a monoacylglyceride of the formula:

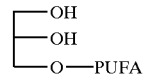

wherein PUFA is defined as in claim 3.

19. Phospholipids enriched with EPA and/or DHA, of the formula:

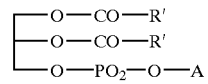

wherein R' is polyunsaturated fatty acid of the n3 series having 2 to 6 double bonds and A is selected from the group consisting of ethanolamine, serine and choline whose EPA and DHA content varies from 40 to 60% of the total fatty acids.

20. Clyceric monoesters enriched with EPA and/or DNA of the formula

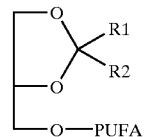

wherein R1 and R2 are lower alkyl and PUFA is polyunsaturated fatty acid having 2 to 6 double bonds whose EPA and DHA content is at least 70% of the total fatty acids.

* * * * *